(12) United States Patent
Östan et al.

(10) Patent No.: US 12,011,341 B2
(45) Date of Patent: Jun. 18, 2024

(54) MEDICAL DRESSING, A MEDICAL DRESSING SYSTEM AND A METHOD OF REDUCING WORKLOAD FOR NURSING PERSONNEL

(71) Applicant: Mölnlycke Health Care AB, Gothenburg (SE)

(72) Inventors: Karin Östan, Nödinge (SE); Niclas Flach, Alingsås (SE); Dennis Hansson, Gunnilse (SE); Magnus Persson, Gothenburg (SE); Shiva Eibpoosh, Gothenburg (SE); David Valham, Västra Frölunda (SE); Elin Näsström, Sandared (SE)

(73) Assignee: MOLNLYCKE HEALTH CARE AB, Gothenburg (SE)

( * ) Notice: Subject to any disclaimer, the term of this patent is extended or adjusted under 35 U.S.C. 154(b) by 254 days.

(21) Appl. No.: 16/312,227

(22) PCT Filed: Jun. 14, 2017

(86) PCT No.: PCT/EP2017/064544
§ 371 (c)(1),
(2) Date: Dec. 20, 2018

(87) PCT Pub. No.: WO2017/220404
PCT Pub. Date: Dec. 28, 2017

(65) Prior Publication Data
US 2019/0192351 A1  Jun. 27, 2019

(30) Foreign Application Priority Data
Jun. 23, 2016  (EP) .................................... 16176002

(51) Int. Cl.
*A61F 13/00* (2024.01)
*A61F 13/0206* (2024.01)
*A61F 17/00* (2006.01)

(52) U.S. Cl.
CPC .... *A61F 13/00085* (2013.01); *A61F 13/0206* (2013.01); *A61F 17/00* (2013.01);
(Continued)

(58) Field of Classification Search
CPC ................ A61F 13/00; A61F 13/00008; A61F 13/00021; A61F 13/00085; A61F 13/02;
(Continued)

(56) References Cited

U.S. PATENT DOCUMENTS

| 4,399,816 A | 8/1983 | Spangler |
| 4,468,227 A | 8/1984 | Jensen |

(Continued)

FOREIGN PATENT DOCUMENTS

| ES | 1078038 | 11/2012 |
| WO | 2008149107 | 12/2008 |
| WO | 2014060625 | 4/2014 |

OTHER PUBLICATIONS

3M Tegaderm Absorbent Clear Acrylic Dressing, [online] 2015 [retrieved from website, https://multimedia.3m.com/mws/media/2917500/tegaderm-absorbent-clear-acrylic-dressing-sell-sheet.pdf (Year: 2015).*

(Continued)

*Primary Examiner* — Alireza Nia
*Assistant Examiner* — Gina McCarthy
(74) *Attorney, Agent, or Firm* — Kilpatrick Townsend & Stockton LLP

(57) ABSTRACT

A medical dressing for application at a treatment area of a human body is provided. The dressing comprises a border area surrounding a central inspection area which is intended (Continued)

to be placed over said treatment area. The dressing also comprises a pad which may be arranged in the central inspection area and may be at least partly removed from the central inspection area for enabling visual inspection of the treatment area. There is also provided a medical dressing system and a method for reducing the workload for nursing personnel.

14 Claims, 4 Drawing Sheets

(52) U.S. Cl.
CPC ............... *A61F 2013/00272* (2013.01); *A61F 2013/00404* (2013.01); *A61F 2013/00817* (2013.01)

(58) Field of Classification Search
CPC ............... A61F 13/0206; A61F 13/023; A61F 13/0266; A61F 13/069; A61F 2013/00089; A61F 2013/00182; A61F 2013/00272; A61F 2013/00361; A61F 2013/00404; A61F 2013/00557; A61F 2013/0057; A61F 2013/00817; A61F 2013/00846; A61F 2013/15024; A61F 15/00; A61F 15/006; A61F 15/008; A61F 13/0203; A61F 13/0213; A61F 13/022; A61F 13/0246; A61F 13/0279; A61F 13/05; A61M 25/02; A61L 15/60
See application file for complete search history.

(56) References Cited

U.S. PATENT DOCUMENTS

| | | | | |
|---|---|---|---|---|
| 4,917,112 A | * | 4/1990 | Kalt | A61F 13/023 D24/189 |
| 5,056,510 A | * | 10/1991 | Gilman | A61F 13/0246 D24/189 |
| 5,086,763 A | * | 2/1992 | Hathman | A61F 13/0206 602/42 |
| 5,562,107 A | | 10/1996 | Lavender et al. | |
| 5,702,356 A | | 12/1997 | Hathman | |
| 5,704,905 A | * | 1/1998 | Jensen | A61F 13/0213 602/42 |
| 5,792,089 A | * | 8/1998 | Penrose | A61F 13/0203 602/57 |
| 5,994,613 A | * | 11/1999 | Cummings | A61F 13/022 602/58 |
| 7,135,606 B1 | * | 11/2006 | Dozier | A61F 13/0203 602/56 |
| 2005/0215932 A1 | * | 9/2005 | Sigurjonsson | A61L 15/60 602/54 |
| 2008/0039759 A1 | * | 2/2008 | Holm | A61F 13/0226 602/41 |
| 2010/0204667 A1 | * | 8/2010 | Chakravarthy | A61F 13/0279 604/385.03 |
| 2012/0197206 A1 | * | 8/2012 | Glenn | A61M 25/02 604/174 |
| 2019/0167483 A1 | * | 6/2019 | Simmons | A61F 13/05 |

OTHER PUBLICATIONS

3M Tegaderm Absorbent Clear Acrylic Dressing, [online] 2015 [retrieved on Apr. 18, 2022] retreived from website https://multimedia.3m.com/mws/media/291750O/tegaderm-absorbent-clear-acrylic-dressing-sell-sheet.pdf (Year: 2015).*
Chinese Application No. 201780039027.3, Office Action dated Aug. 18, 2020, 9 pages.
European Application No. 16176002.0, Extended European Search Report dated Nov. 3, 2016, 6 pages.
PCT Application No. PCT/EP2017/064544, International Preliminary Report on Patentability dated Jan. 3, 2019, 7 pages.
PCT/EP2017/064544, "International Search Report and Written Opinion", dated Jul. 7, 2017, 8 pages.

* cited by examiner

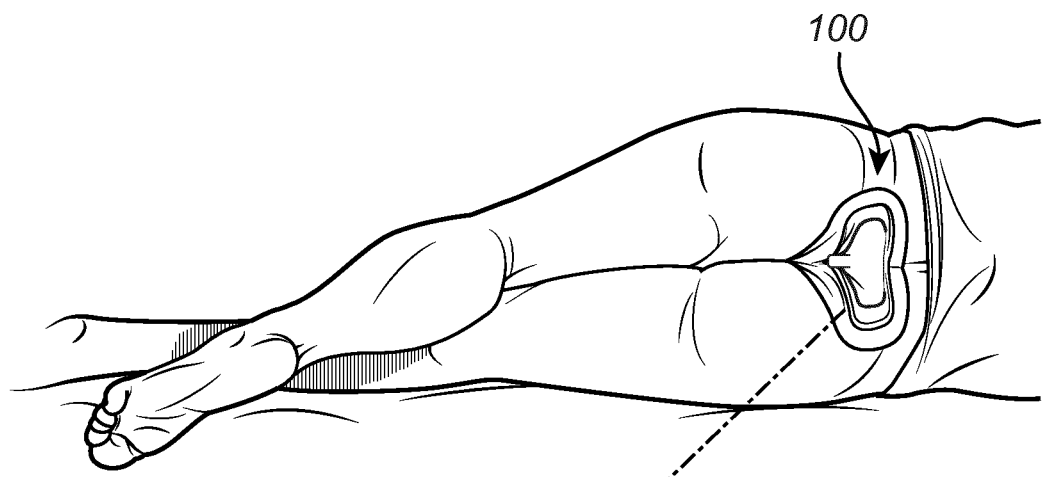
Fig. 1
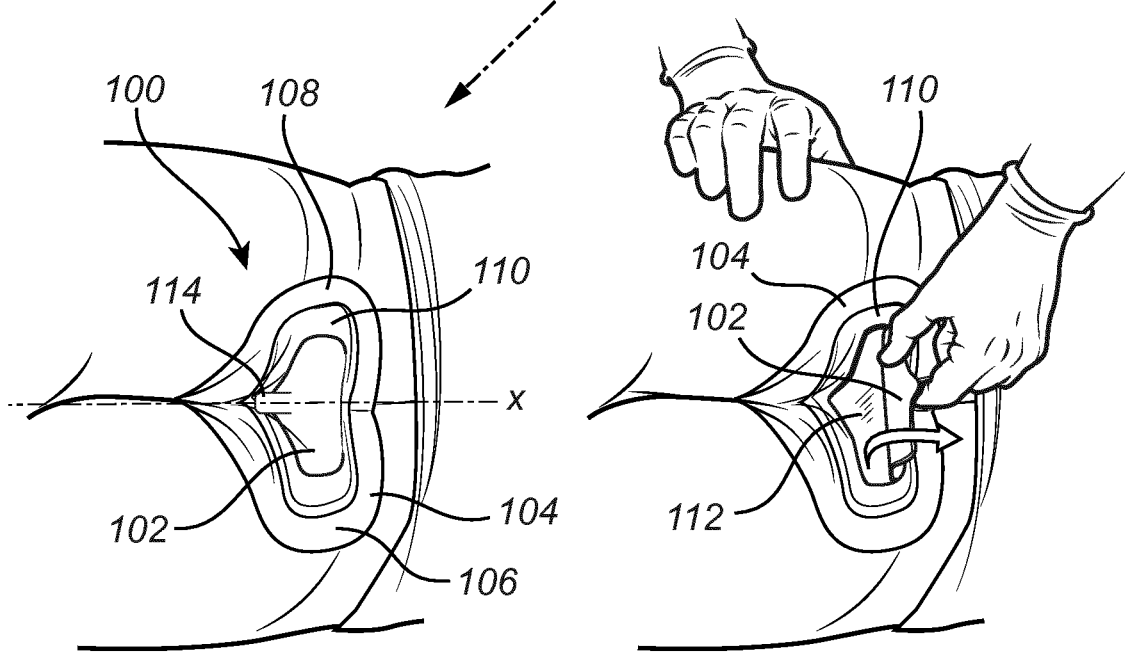
Fig. 1a
Fig. 1b

MEDICAL DRESSING, A MEDICAL DRESSING SYSTEM AND A METHOD OF REDUCING WORKLOAD FOR NURSING PERSONNEL

TECHNICAL FIELD

The present invention relates to a medical dressing for application at a treatment area of a human body. The invention also relates to a medical dressing system comprising such a medical dressing. Furthermore, the invention relates to a method of reducing workload for nursing personnel.

BACKGROUND ART

Pressure ulcers very often arise among persons being bedridden for various reasons, such as for instance due to long term hospitalization or other causes of immobility. Not only does a pressure ulcer cause great discomfort and/or pain to the affected person, but it also causes difficulties to nursing personnel and other care-takers.

It is therefore desirable in, for instance, hospitals to act proactively rather than reactively. In other words, instead of waiting for pressure ulcers to develop and then perform treatment, it is preferred to try to prevent the pressure ulcers from even occurring.

Pressure ulcers are largely preventable. When pressure ulcers occur, they can become painful wounds that require months to heel. The prevention of pressure ulcers includes inspection of the skin, control of risk factors, keeping the skin clean and dry, and redistributing pressure over high risk bony areas.

To date, such preventative means typically include pressure off-loading or re-positioning the patient at regular intervals such that pressure is relieved or re-distributed, and the amount of pressure that the individual is exposed to is minimized.

Where a pressure sore has started to develop, or where it is expected to develop, nursing personnel may place a padded dressing onto the skin area. The nursing personnel needs to check from time to time to examine the skin underneath the dressing, and to see if a pressure ulcer has developed.

The inspection of the skin area requires the dressing to be opened up, and detached from the skin. One option is, of course, to remove the dressing and apply a new dressing after having checked the relevant skin area. However, this is both costly and time consuming. Alternatively, nursing personnel may detach the dressing slightly by gripping and lifting an adhesive border of the dressing (i.e. the portion of the dressing surrounding the pad) so that the relevant skin area can be checked, and then the dressing is re-applied by re-attaching the adhesive border to the surrounding skin. Although this is cost effective and less time consuming than removing the old dressing and applying a new dressing, there are some drawbacks.

One drawback is that the border loses some of its adhesive capability (stay-on ability) each time it is detached. An improperly adhered dressing also risks reducing the pressure ulcer prevention capability of the dressing. Furthermore there is a risk that the border will become wrinkled when detached and re-applied, which also reduces the adhesive capacity. Additionally, there is a risky that such wrinkles turn into compartments for body fluids (such as sweat) which in turn may lead to such compartments growing as more fluid is accumulated, therefore further reducing the stay-on ability of the dressing. Eventually, the nursing personnel will, due to the resulting reduced stay-on ability, need to replace the old dressing with a new one.

SUMMARY OF THE INVENTION

An object of the present invention is to alleviate the drawbacks of the prior art. This and other objects, which will become apparent in the following are accomplished by the accompanying claims.

The present invention is based on the realization that by allowing at least a partial decoupling of a pad of a medical dressing from a surrounding border, the border does not have to be detached from the skin for inspection purposes and therefore the adhesive capability of the border is not impaired. In particular, the inventor has realized that the stay-on ability of a medical dressing can be retained by (instead of starting to lift the border) lifting or tilting the pad without needing to detach the border. This will result in longer stay-on ability of the medical dressing and less frequent need for replacing an old dressing with a new one. Furthermore, the handling of the dressing becomes easier for the nursing personnel when inspecting whether or not any pressure ulcers have developed. Thus, the present invention provides for beneficial technological and economical progress in the field of pressure ulcer prevention.

According to at least a first aspect of the invention, there is provided a medical dressing for application at a treatment area of a human body. The medical dressing comprises an annular border area comprising a film having
    a body-facing proximal side provided with an adhesive layer for adhering the border area to skin surrounding said treatment area, and
    an opposite distal side,
a central inspection area for alignment with said treatment area, the central inspection area being surrounded by said border area, and
a pad movable between at least two states:
    a first state in which the pad is located in the central inspection area, and
    a second state in which the pad is at least partly removed from the central inspection area for enabling visual inspection of said treatment area.

It should be understood that in this application the term "treatment area" does not necessarily imply an injured, bruised, wounded or ulcerated area, but may on the contrary refer to an intact area of the human body onto which the medical dressing is placed for preventive purposes. Thus, the treatment performed by a caregiver may be a prophylactic treatment.

The medical dressing is particularly useful for pressure ulcer prevention and/or pressure ulcer mitigation. The pad, which is suitably made of a material providing a pressure relieving function, can be at least partly lifted for allowing the treatment area to be visually (and as an option also tactilely) inspected. The lifting action may suitably be performed completely independent of the border area, which means that the border area may stay adhered to the skin surrounding the treatment area while the state of the pad is shifted.

The present inventive concept allows for visual inspection of the skin area by at least partly removing the pad from the central inspection area of the medical dressing.

The border area is annular, which means that it forms a closed curve/path around the rest of the dressing. Although the annular border area may be circular or substantially circular, it should be noted that other annular shapes of the border are conceivable. For instance, the annular border area may form various types of curved paths or may even present non-curved straight side or sides. For instance, embodiments suitable for application onto the sacral area may have an annular border area forming a substantially heart-shaped path. Furthermore, in some embodiments, the annular border area may be provided with a notch or indentation at the outer perimeter of the border area, which in some cases may facilitate application of the dressing around certain skin areas, such as for instance at the gluteal cleft. Furthermore, in some embodiments, the annular border area may be provided with one or more tab portions projecting outwardly from the rest of the border area. In this connection it should be understood that inwardly means a direction towards the inner perimeter of the border area, i.e. a direction towards the pad, while outwardly is an opposite direction. Other shapes are also conceivable. For instance, for embodiments which are intended for the heel, the annular border area may form an hourglass or butterfly contour.

In at least some exemplary embodiments, the border area defines a boundary of the central inspection area, while in other exemplary embodiments the central inspection area is defined by a raised wall portion which is surrounded by the border area. Allowing a border area to define the central inspection area may enable the production of a compact medical dressing. The production processes may include a first step in which a body contact layer (e.g. film coated with adhesive as described herein) which has been provided with a pre-cutout inspection hole is applied onto a backing layer. This will form the border area. Alternatively, the backing layer may be omitted and a thicker body contact layer may be used. In a second step a pad is applied to cover the inspection hole (which will thus form a central inspection area). The pad may suitably be provided with a narrow border portion. In an optional third step, one side of the pad is connected to the border area, e.g. by ultrasonic and/or heat welding or by use of a construction adhesive such as acrylic glue, thereby obtaining a hinged connection. It the pad is provided with a narrow border portion, that border portion may be connected to the border area of the medical dressing. In order to avoid unintentional lifting of the pad from the central inspection area, the pad may suitably be provided with attachment means, such as a tape which can be attached to the border area (or any other type of attachment means described in this specification).

As will be discussed in more detail further below, the central inspection area may comprise a hole, such as a through hole or a blind hole. According to at least some exemplary embodiments, in said first state, at least a portion of the pad is located in said hole (be it a through hole or a blind hole). Thus, the pad would not just be a lid on top of the hole, but actually (at least partly) sunk into the hole. This is advantageous as the pad will provide a good pressure reducing function. According to at least some exemplary embodiments of the invention, a major portion of the thickness of the pad is located in said hole. According to at least some exemplary embodiments the entire pad is located in said hole.

In some embodiments, the annular border area may be substantially heart-shaped and symmetrical about a geometrical axis of symmetry of the medical dressing. The axis of symmetry is located at a part of the dressing which will normally be applied in the gluteal cleft. The border area may comprise a first lobed portion on one side of said axis of symmetry and a second lobed portion on the other side of said axis of symmetry. The border area may be substantially heart shaped such that said first and second lobed portions form part of the lobed upper sides of a heart shape. The first and second lobed portions may be separated by a forked portion which replaces the pointed lower part of a heart shape. The forked portion of the border area may comprise a protrusion on either side of an interstice located coaxially with the axis of symmetry. Such a configuration is believed to improve the conformity to the sacral area of human body.

In the field of medical dressings, in particular, wound dressings, a film provided with an adhesive layer for adhering to the patient is often referred to as a wound contact layer. The present invention is primarily intended for pressure ulcer prevention, i.e. for use on a human body area which has no wound. Therefore, in this application the combined film and adhesive layer will be referred to as a body contact layer. However, it should be understood that although the primary use of the invention is pressure ulcer prevention, if nursing personnel decides to use it as a wound dressing the body contact layer could be applied onto a wound.

In this application directional terms such as "proximal" or "proximally" and "distal" or "distally" are used. These terms are referenced with respect to the intended placement on a treatment area of a human body. In other words, the most proximal portion of the medical dressing is the portion that is intended to be nearest treatment area. The most distal portion is the portion that is intended to be furthest away from the treatment area. For instance, the adhesive layer will be proximal to the film.

The central inspection area may be embodied in different ways to enable visual inspection of the treatment area. In some example embodiments, the central inspection area comprises a through hole. In some example embodiments, the central inspection area comprises a blind hole. For instance a transparent film may be provided at the proximal end of the central inspection area. When the pad has been at least partly removed from the central inspection area, the transparent film may suitably be cleaned if it has become soiled by body exudates, thereby improving visual inspection. The dressing with the cleaned film may then be reused with the same pad or with a new pad. In some example embodiments, said transparent film may be in one piece with the film forming part of the border area. Thus, the medical dressing may be provided with a body contact layer which extends over the border area as well as the central inspection area. These various alternatives may be implemented for a medical dressing regardless if the central inspection area is defined by the border area or by a raised wall portion surrounded by the border area.

Other advantages of having a film or body contact layer extending across the central inspection area include protection of the skin when the pad is lifted for inspection, improved stay-on ability of the medical dressing since substantially no pulling force is applied at an adhesive edge. The pad may be provided suitably be provided with an adhesive. With a film present in the central inspection area, a stronger adhesive may be provided on the proximal side of the pad than if the pad would be in direct contact with the skin, thus allowing for a good stay-on ability of the pad.

A central inspection area in the form of a through hole, i.e. without a film extending across the central inspection area, may be desirable, for certain kinds of skin care regimes in which skin creams are used. Such a central inspection area will also facilitate palpating for the nursing personnel, for instance to detect raised skin temperature, which may be an indication of a developing ulcer.

In at least some example embodiments the at least partly removable pad is attached to surrounding portion or portions of the medical dressing by means of separate attachment means. Such attachment means may, for instance, be a sticker or a hook and look type of fastening. As mentioned previously the surrounding portions may be the border area or a raised wall portion, either one being configurable for defining the central inspection area. In at least some example embodiments the at least partly removable pad is attached to surrounding portion or portions of the medical dressing by common material portions, e.g. acting as a hinge. However, in other embodiments the at least partly removable pad may be produced as a separate piece and may be subsequently connected by means of welding and/or gluing.

The portion or portions surrounding the central inspection area may suitably comprise a raised portion of the medical dressing. This is reflected in at least one example embodiment, according to which said film lies in a first geometrical plane, the dressing further comprising a wall portion projecting distally from said first geometrical plane, wherein the wall portion at least partly defines said central inspection area. In at least some example embodiments the wall portion forms a frame around the central inspection area and around the pad. Similarly, the border area may be considered as forming a frame around the wall portion, the pad and the central inspection area. Thus, in at least some example embodiments, the pad, the wall portion and the border area may be arranged substantially coaxially.

According to at least one example embodiment, one of the outer perimeter of the pad, the outer perimeter of the wall portion and the outer perimeter of the border area is substantially conformal with at least another one of the outer perimeter of the pad, the outer perimeter of the wall portion and the outer perimeter of the border area. According to at least one example embodiment all three outer perimeters are substantially conformal. According to at least one example embodiment, although the border area may be substantially conformal with the pad and/or the wall portion, the border area may be provided locally with small projecting tabs or indentations/notches.

According to at least one example embodiment, said border area has an outer perimeter and an inner perimeter, wherein the inner perimeter borders to said wall portion. The distal end of the wall portion may lie in a second geometrical plane which is parallel to said first geometrical plane. Suitably, the border area is proximally spaced from the second geometrical plane. In other words, the thickness of the border area is suitably smaller than the thickness of said wall portion.

According to at least one example embodiment, said pad is attached or attachable to said wall portion at least in said first state, i.e. the state in which the pad is located in the central inspection area. Thus, in at least some example embodiments, after the pad has been moved to the second state for enabling visual inspection of the treatment area, the pad may be re-attachable to said wall portion in order to again reach the first state. In other example embodiments, a new pad may be attached to the wall portion after a used pad has been moved to its second state. In some example embodiments, the pad stays attached to the wall portion when changing between the first state and the second state. The pad may, for instance, stay attached to the wall portion by means of a hinge element which may be a separate or an integrated part of the wall portion and the pad, or by means of other types of attachment means.

According to at least one example embodiment, said pad is provided with releasable attachment means for attaching said pad to said wall portion, wherein releasing said attachment means enables the pad to be moved from said first state to said second state of the pad, wherein the attachment means allows re-attachment of said pad to said wall portion when said pad is moved back to said first state. Examples of such releasable attachment means are stickers, tapes or hook and loop type of fastening means.

According to at least one example embodiment, a distal end surface of said wall portion and a distal end surface of said pad lie in a common second geometrical plane, said second geometrical plane being parallel with said first geometrical plane. Such a configuration may be beneficial for returning the pad to its first state and re-attaching the pad to the wall portion after visual inspection has been carried out. Furthermore, by providing a substantially even distal end surface of the medical dressing, undesired pressure points are avoided since the distal ends of the pad and wall portion lie in a common geometrical plane.

According to at least one example embodiment, said pad is a cutout from said wall portion. Thus, the pad and the wall portion may be made from the same starting material or blank, from which the pad is cut out. Put differently, the pad and the wall portion may be obtainable from one common piece. For instance, the common piece may comprise an absorption layer and a backing layer distally to the absorption layer. The common piece from which the wall portion is made and the pad is cut out may also comprise other layers, such as a liquid distributing layer. It should therefore be understood that, in at least some example embodiments, the wall portion and the pad may be made in the same material or materials. Furthermore, it is not only the material that may be the same, but also the composition, density and/or layering, etc. may be the same in the pad as in the wall portion. Although, these example embodiments are advantageous from a manufacturing perspective, in at least some other example embodiments, the pad and the wall portion may be made from different pieces of material or from materials having different composition, density and/or layering. In other example embodiments, the pad could be manufactured separately and applied in a separate step to the rest of the wound dressing. The pad may be manufactured by ultrasonic cutting/welding, wherein layers of the pad are welded together forming a closed structure.

Although the wall portion may advantageously be of the same material as the pad, in at least some embodiments, the wall portion may be of a different material. For instance, the wall portion may be of a foam material which is easy to shape and cut, and is conformable. The wall portion could be made of different gels (e.g. silicone, acrylic hydrogels or similar) which provide good pressure distribution.

In at least some example embodiments the wall portion may be bevelled. The wall portion may suitably have its thicker portion nearest the central inspection area, and slanting to a thinner portion towards the surrounding border area. This may reduce the risk of peak pressures due to sharp edges and provide a good pressure gradient.

As mentioned previously, the central inspection area may comprise a hole. It should therefore be understood that in embodiments having a wall portion defining said central inspection area, said wall portion may define a central hole included in said central inspection area. Similarly to the previous discussion, such a central hole may be a through hole or a blind hole. If it is a blind hole, the bottom of said blind hole may be formed by a film, such as the film which is also present at the border area. It should be understood that the wall portion may form a frame around the central hole, i.e. it may be annular.

As mentioned previously, the body contact layer may extend over the central inspection area. In at least some example embodiments, a more general description is suitable, namely that said film at the border area extends into and across the central inspection area. Thus, this means that the film may be provided with an adhesive layer over substantially the entire extension of the film. However, this also means that in some other example embodiments, it is conceivable that only peripheral areas of the film are provided with the adhesive layer. For instance, only the film at the border area is provided with an adhesive layer, while the portion of the film interfacing proximally to the wall portion is void of adhesive layer. In some example embodiments only the portion of the film covering the hole of the inspection area is void of adhesive layer while the portion of the film at the border area and the portion of the film interfacing proximally to the wall portion are provided with the adhesive layer.

According to at least one example embodiment, the body contact layer is perforated, wherein perforations extend from the distal to the proximal side of the body contact layer. Thus, in such cases the film provided with the adhesive layer is a perforated film, and the adhesive layer is a perforated adhesive layer. The perforations in the film may form a regular pattern. This allows any body exudates or other moisture to be transported away from the skin. However in other embodiments the film is not perforated. A non-perforated film may provide better adhesion to the skin, and avoids one process step during production.

According to at least one example embodiment the film coated with the adhesive layer is a plastic film. Suitable materials for the plastic film include, but are not limited to, breathable polyolefin-based films (such as, e.g. polyethylene), polyamide, polyurethane, polyester and silicone. The film may have a thickness of from 15 to 100 μm, e.g. from 30 to 70 μm, e.g. from 45 to 60 μm. Suitably, the film is a thin polyurethane film.

According to at least one example embodiment, the adhesive layer comprises a hydrophobic material. Examples of suitable adhesives include, but are not limited to, silicone gels, hot melt adhesives, acrylate adhesives, polyurethane gels, and hydrocolloid adhesives. In some embodiments, the adhesive is comprised of a material that is non-irritating to skin, for example, a silicone gel. Examples of suitable silicone gels include the two-component RTV systems such as Q72218 (Dow Corning) and SilGel 612 (Wacker Chemie AG) mentioned herein, as well as the NuSil silicone elastomers. In embodiments of the invention, the adhesive may comprise a silicone gel. For example, the adhesive may comprise a soft silicone gel having as softness (penetration) of from 8 to 22 mm, such as for example from 12 to 17 mm, as measured by a method based on ASTM D 937 and DIN 51580.

According to at least one example embodiment, the medical dressing comprises a backing layer, which will generally be the most distal component of the wound dressing. The backing layer may typically be a thin film, sheet, or membrane that is vapour permeable and waterproof. Examples of suitable materials for the backing layer include, but are not limited to, polyurethane films, silicone films, polyester-based nonwoven materials, and laminates of polyester-based nonwoven materials and polyurethane films. The backing layer may be bonded to the pad, the wall portion and/or the body contact layer (i.e. the film coated with adhesive on the proximal side), for example, via an adhesive such as a pressure sensitive adhesive (such as an acrylic adhesive). In at least some embodiments, the backing layer is co-extensive with the body contact layer in that both layers have the same outer dimensions, and is bonded to the distal side of the film in the border area of the medical dressing.

According to at least one example embodiment, the pad comprises a material that provides for good pressure distribution and fluid handling. For example, the pad may comprise an absorbent, conformable material such as, for example, foams and/or cellulose-based materials. The pad may comprise a hydrophilic material, e.g., a hydrophilic foam. Suitable foam materials include, but are not limited to polyurethane foams. In some embodiments, the pad comprises a porous foam. In some embodiments, the pad is a multilayered pad. For example, the pad may comprise two or more layers having different properties laminated together. For example, the pad may comprise a first absorbent layer on its proximal side and a second absorbent layer on its distal side, with the second absorbent layer being affixed to the backing layer. In some such embodiments, another layer is disposed between the first absorbent layer and the second absorbent layer, for example, a liquid distributing layer, which can act to spread liquid absorbed by the first absorbent layer and transmit the liquid to the second absorbent layer. In some embodiments, the first absorbent layer is comprised of a foam, for example, a hydrophilic foam such as a hydrophilic polyurethane foam. In some embodiments, the second absorbent layer comprises a superabsorbent material, such as superabsorbent fibers (SAF) or superabsorbent polymers (SAP). For example, polyacrylic super-absorbent fibers may be suitable. The second absorbent layer may also comprise binding fibers, non-limiting examples of which include polyester fibers, polyethylene fibers, polypropylene fibers, and blends thereof. Alternatively or additionally, the second absorbent layer may comprise cotton fibers. In some embodiments, the liquid distributing layer is thinner than both the first and second absorbent layers. In some embodiments, the liquid distributing layer is comprised of a nonwoven material, such as, for example, viscose, polyester, or both.

In at least some example embodiments, the pad or at least one of the layers of the pad comprises an absorbent material which has a free swell absorptive capacity, corresponding to the maximum absorptive capacity, of at least 3 times its own weight as measured by EN 13726-1:2002, preferably at least 5 times its own weight as measured by EN 13726-1:2002 and more preferably at least 8 times or at least 10 times as measured by EN 13726-1:2002.

When the medical dressing has been applied at the treatment area of the human body, it is desirable to have a good stay-on ability of the actual pad, so that it can provide its desired effect on to the treatment area (i.e. reduce the risk of a pressure ulcer developing). While one should strive for a good stay-on ability of the pad, the nursing staff should also be allowed to lift the pad and then place it back to its first state for a repeated number of times. Such a stay-on ability may be provided in different ways.

In embodiments in which a film extends across the proximal end of the central inspection area, the pad is suitable provided with an adhesive for temporarily adhering the pad to the distal side of the film in the central inspection area. According to at least one example embodiment, the total adhesion energy between the pad and the film is lower than the total adhesion energy between the film and the skin. This is to avoid the medical dressing from loosening from the skin. However, it should be noted that the adhesion per area unit does not necessarily have to be higher between the film and the skin compared to the adhesion per area unit between the pad and the film, as long as the total adhesion energy is higher. The adhesion between the film and the skin may be provided by the herein discussed adhesive layer which together with the film forms the body contact layer.

The adhesive strength between the pad and the film, as well as between the film and the skin may be 0.2-4 N, suitably between 1-3 N, the adhesive strength being measured on 25 mm strips against steel using a 90 degree peel test (ASTM D3330//D3330M-04, method F, wherein the mean load was measured between 25 and 75 mm and the resting time after calendaring was 1 minute).

The adhesive material for adhering the pad to the distal side of the film may be in the form of silicones, hot melts, acrylates, rubber-based, polyurethane-based.

In embodiments in which the central inspection area is a through hole, i.e. without a film extending across the central inspection area, the pad may suitably be temporarily adhered to the naked skin by appropriate adhesive materials such as hydrogels, or any one of the above mentioned adhesive materials used for adhering to a film, as long as they are skin-friendly.

Regardless of the pad being designed for temporary adhesion to a film or to the naked skin, the adhesive may be provided all over the proximal surface of the pad or in different patterns across the proximal surface of the pad.

According to at least one example embodiment, the medical dressings comprises a release layer, intended to be removed before use. The release layer may be disposed on and releasably attached to the proximal side of the body contact layer. By "releasably attached," it is meant that the release layer may be peeled away from the rest of the medical dressing by hand. The release layer acts as a barrier that can protect the sterility of the pad and any adhesive present on the proximal surface of body contact layer (and any adhesive present on the backing layer and pad depending on their extension relative to the body contact layer) before the dressing is used. The release layer may be made of any of a variety of suitable materials known in the art, such as, for example, polyethylene, polyester, polypropylene, and silicone-coated paper.

From the above, it should be understood that, the proximal side of the pad may be provided with adhesive. This may, for instance, be the case when said central inspection area defines a through hole, in which case the pad may be adhered to the treatment area. The adhesive may be any one of the above mentioned skin-friendly adhesive materials. A pad provided with an adhesive may also be conceivable in which the central inspection area defines a blind hole having its proximal end occluded by a film portion, in which case the pad may temporarily be adhered to the distal side of such a film portion.

According to at least a second aspect of the invention, there is provided a medical dressing system. The medical dressing system comprises a medical dressing according to any embodiment of the first aspect of the invention, wherein said pad is provided in said first state or as a separate component for subsequent placement in said first state. Thus, the medical dressing system allows for the provision of a complete ready-to-use medical dressing in which the pad is already in the first state of the medical dressing, i.e. already located in the central inspection area. However, the medical dressing system also allows for the provision of a kit of components, in which the pad is one component and the rest of the medical dressing, including the border area and the central inspection area, is provided as another component to which the pad may be assembled. The pad may suitably be assembled to the rest of the medical dressing by any suitable attachment means, such as an attachment means of the type exemplified previously.

According to at least one example embodiment of the medical dressing system, said pad is a first pad, the system further comprising a replacement pad for replacing the first pad while the medical dressing is still applied to a human body without requiring removal of the border area from the skin of the body. In other words, when the first pad has been used, e.g. soiled, it may be discarded and replaced by a fresh replacement pad. The border area may be left unaffected, thus not compromising the stay-on ability of the dressing. If the central inspection area comprises a blind hole having its proximal end covered by a film portion, the film portion may suitable be cleaned before the replacement pad is inserted into the blind hole.

According to at least a third aspect of the invention, there is provided a method of reducing workload for nursing personnel. The method comprises providing a replacement pad for enabling the nursing personnel to replace a used pad comprised in a medical dressing according to any embodiment of the first aspect or a medical dressing system according to any embodiment of the second aspect with said replacement pad, without requiring removal of the border area from the skin of the body. This will facilitate for the nursing personnel to avoid replacing the entire medical dressing, since only the pad needs to be replaced. It is considered much easier to place a replacement pad to the central inspection area of an applied medical dressing, then applying an entire new dressing to a patient (not the least because of the challenge involved in applying the border area as wrinkle free as possible). Furthermore, even if eventually, the nursing personnel decides to change the entire medical dressing after a number of replacement pads have been used, such a change will be made much more seldom then with the prior art dressings, in which the border area needs to be lifted for visual inspection.

BRIEF DESCRIPTION OF THE DRAWINGS

FIG. 1 shows a medical dressing according to at least one exemplary embodiment of the invention, the medical dressing having been applied at a treatment area of a human body.

FIG. 1a is a detailed view of FIG. 1.

FIG. 1b is a detailed view of the medical dressing in FIGS. 1 and 1a, illustrating an inspection of the treatment area.

DETAILED DESCRIPTION OF THE DRAWINGS

Figure 2:
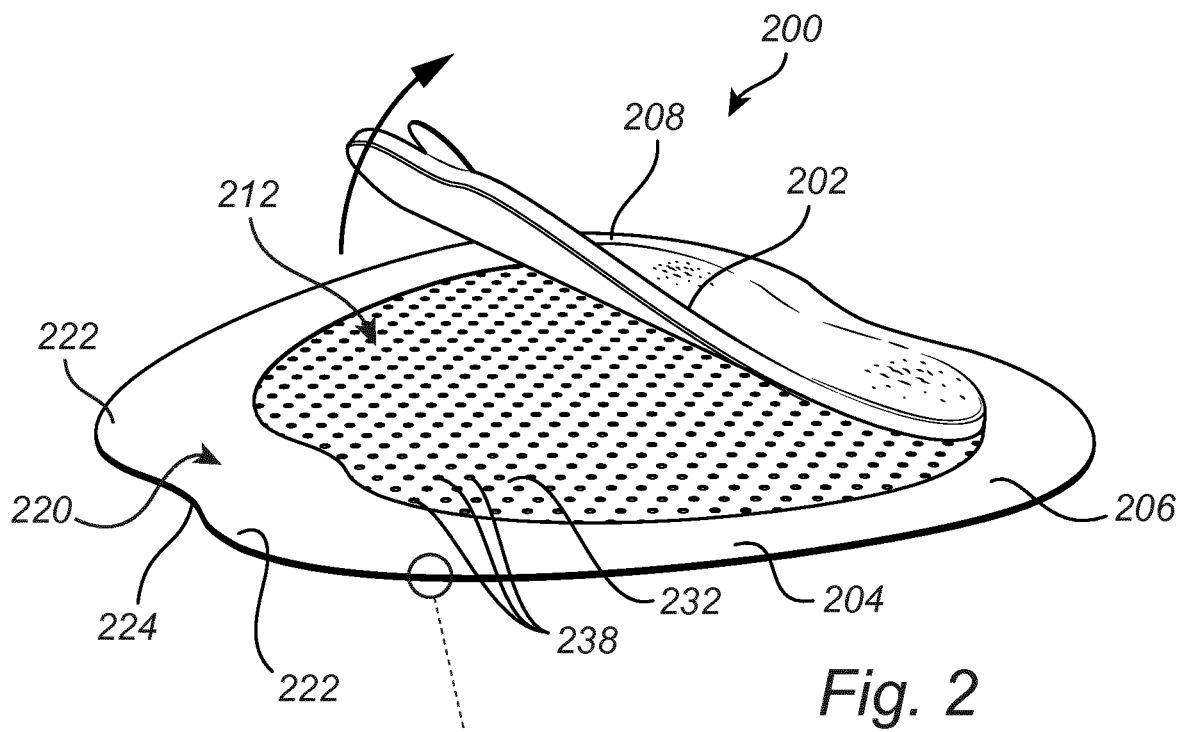
FIG. 2 shows a medical dressing according to at least one exemplary embodiment of the invention, in which a pad is partly removable from a central inspection area for enabling visual inspection of a treatment area.

FIG. 1 shows a medical dressing 100 according to at least one exemplary embodiment of the invention, the medical dressing 100 having been applied at a treatment area of a human body. In this figure, the medical dressing 100 has been applied to the gluteal cleft, however, the inventive concept can be readily implemented on other areas of the human body.

FIGS. 1a and 1b are detailed views illustrating the general principal of the inventive concept. The medical dressing 100 comprises a pad 102 which covers an area of the human body where development of a pressure ulcer may occur. Normally, the pad 102 is opaque. The pad 102 is a preventive measure, which reduces the risk of pressure ulcers developing at the area covered by the pad 102. The pad 102 is, therefore, suitably made of a pressure relieving material, such as materials exemplified previously in this specification. The pad 102 is appropriately adapted to the gluteal cleft by being designed as a substantially heart-shaped pad. However, other shapes are also conceivable. In the illustrated embodiment, the medical dressing 100 is symmetrical on either side of a geometrical axis of symmetry X.

The pad 102 is surrounded by an annular border area 104, i.e. a border area 104 which forms a closed curve. The border area 104 comprises a first lobed portion 106 on one side of said axis of symmetry X and a second lobed portion 108 on the other side of said axis of symmetry X. The border area 104 may be substantially heart shaped such that said first and second lobed portions 106, 108 form part of the lobed upper sides of a heart shape. Although in the illustrated embodiment the border area 104 may be regarded as following the contours of a general heart shape, in other embodiments, as previously exemplified, the border area may have other shapes.

The border area 104 comprises a film which has a body-facing proximal side provided with an adhesive layer for adhering the border area to the skin surrounding the treatment area. The opposite side of the film is referred to as the distal side. The distal side of the film may, in at least some embodiments, be attached to a backing layer. Such a backing layer may or may not cover also the pad 102.

In-between the border area 104 and the pad 102, there is provided a wall portion 110 of the medical dressing 100. The wall portion 110 projects distally from the geometrical plane of the film. In FIGS. 1a-1b the wall portion 110 forms a frame and defines a central inspection area 112 (see FIG. 1b). It should, however, be noted that in other embodiments, the wall portion 110 does not necessarily form a complete closed curve (in the figure following a substantially heart-shaped contour), but could just partly define the central inspection area. In other embodiments, the wall portion may be completely omitted, wherein the border area may suitably define the central inspection window. Regardless of which one of a wall portion or a border area that forms the boundaries of the central inspection area in the various embodiments, it should be understood that in all embodiments, the border area will surround the central inspection area (either with or without an intermediate wall portion).

If a backing layer is attached to the film at the border area, such a backing layer may also cover and be attached to the wall portion.

In FIG. 1a the medical dressing 100 is in a first state. In this first state the pad 102 is located in the central inspection area 112 (only visible in FIG. 1b), thereby occluding visual inspection of the treatment area. Thus, it should be understood that the central inspection area 112 should be properly aligned with said treatment area.

FIG. 1b is a detailed view of the medical dressing 100 in FIGS. 1 and 1a, illustrating an inspection of the treatment area. The nursing staff has lifted the pad 102 into a second state, in which the pad 102 is at least partly removed from the central inspection area 112, thereby enabling visual inspection of the treatment area. The pad 102 and the wall portion 110 may suitably be formed from the same piece of material and remain attached along a point or line of attachment, even after lifting the pad 102 into the second state.

After inspection, the nursing staff may return the pad 102 to its first state. The pad 102 is suitably provided with an attachment means 114 (see FIG. 1a), such as a tab, a tongue, a sticker or any other suitable means of attachment. Such an attachment means 114 may be coated with adhesive. Rather than having an attachment means 114 on the pad 102, as in the figure, the wall portion 110 could instead or additionally be provided with an attachment means. Furthermore, instead of, or in addition to, an adhesive attachment means, there may be other solutions as well, such as hook-and-loop type of fastening, wherein hooks are present on one of said pad 102 and said wall portion 110 and loops for receiving the hooks are present on the other one of said pad 102 and said wall portion 110.

FIG. 2 shows a medical dressing 200 according to at least one exemplary embodiment of the invention, in which a pad 202 is partly removable from a central inspection area 212 for enabling visual inspection of a treatment area. In FIG. 2, the medical dressing 200 lacks the wall portion 110 in FIG. 1. Instead, it is the border area 204 that delimits the central inspection window 212.

The medical dressing 200 in FIG. 2, is substantially heart-shaped and the border area 204 comprises, similarly to the embodiment in FIG. 1, first and second lobed portions 206, 208. It should be noted that in FIG. 2, the first and second lobed portions 206, 208 are separated by a forked portion 220 which replaces the pointed lower part of a heart shape. The forked portion 220 of the border area 204 comprises a protrusion 222 on either side of an interstice 224 located coaxially with the axis of symmetry. The pad 202 in FIG. 2 may, suitably, have a heart shape which substantially conforms with the heart shape of the border area 204. Similarly, in the embodiment in FIG. 1, the shape of the wall portion 110 and/or pad 102 may substantially conform to the heart shape of the border area 104, which may optionally be provided with a forked portion similarly to the one illustrated in FIG. 2.

Figure 2A:
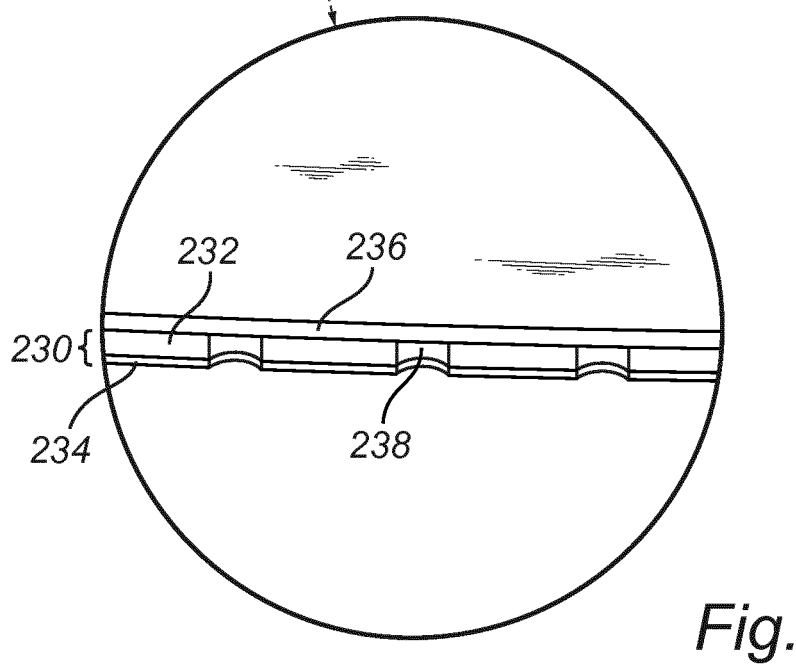
FIG. 2a shows a cross-section of a detail of FIG. 2.

As can be seen in the detailed cross-sectional view of FIG. 2a, the border area comprises a body contact layer 230 which includes a film 232 which on its proximal side is coated with an adhesive layer 234. A backing layer 236 is attached to the distal side of the film 232.

Although the extension of the film 232 may be limited to the border area 204 in some embodiments, in at least some other embodiments (such as shown in FIG. 2), the film 232 does not only form part of the border area 204, but may suitably extend across the entire medical dressing 200, thus also extending across the central inspection area 212. In such cases the body contact layer 230 may be transparent. Thus, the film 232 may be made of a transparent material (and the adhesive layer 234 may also be transparent) so as to enable visual inspection of the treatment area when the pad 202 has been moved from its occlusive first state to its non-occlusive second state. The body contact layer 230 (i.e. film 232 combined with the adhesive layer 234) may suitably be provided with perforations 238 so as to allow moisture to be transported away from the skin. Suitably, the pad 202 may comprise an absorbent material (for instance, distributed in one or more layers of the pad) for absorbing moisture that has traveled through the perforations 238. Before, during or after inspection, the film 232 may suitably be wiped off for improved visibility of the treatment area.

It should be understood that the embodiment of FIG. 2 could be modified so that the film 232 does not extend across the central inspection area 212. The central inspection area 212 could be a through hole. Furthermore, it should be understood that although the embodiment of FIG. 2 illustrates a pad 202 which is only partly removable (the pad 202 remaining partly attached to the medical dressing 200 when lifted/tilted, e.g. remaining attached to a backing layer 236), the medical dressing 200 could be modified so that the entire pad 202 is removable. Examples of embodiments in which the entire pad is removable will be discussed in connection with FIG. 3a and FIG. 3b.

Figure 3A:
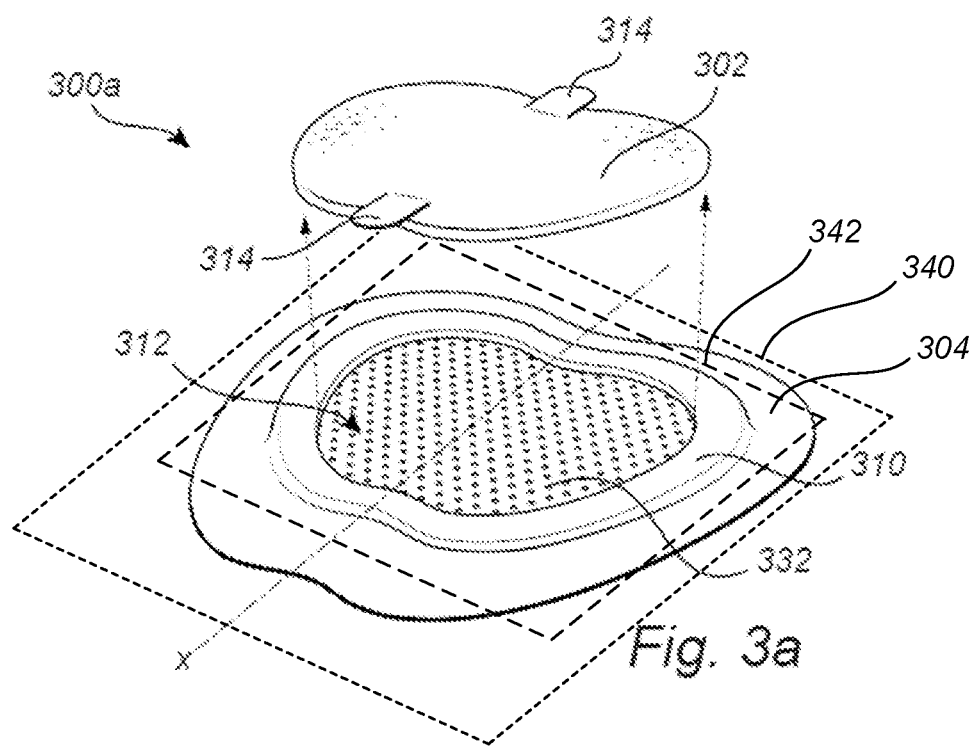
FIGS. 3a and 3b show medical dressings according to at least two exemplary embodiments of the invention, in which a pad is completely removable from a central inspection area for enabling visual inspection of a treatment area.
Figure 3B:
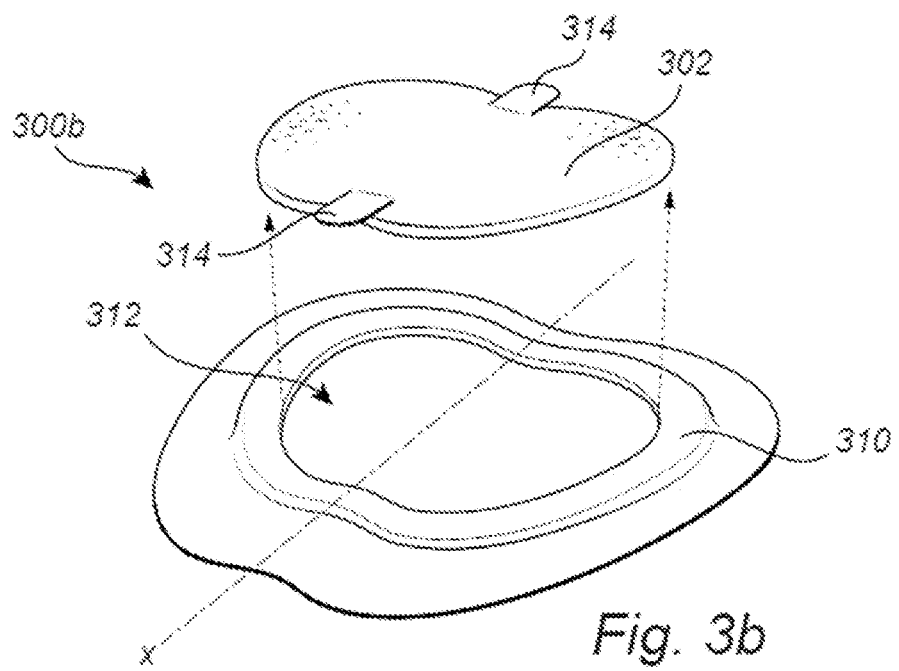

FIGS. 3a and 3b show medical dressings 300a, 300b according to at least two exemplary embodiments of the invention, in which a pad is completely removable from a central inspection area for enabling visual inspection of a treatment area. Features being in common for the two dressings 300a, 300b are denoted with the same reference numerals in FIGS. 3a and 3b.

In FIG. 3a the central inspection area 312 of the illustrated medical dressing 300a is formed as a blind hole, the bottom (proximal end) of the hole being covered by a perforated film 332 extending across the central inspection area 312, similarly to the central inspection area 212 of the dressing 200 illustrated in FIG. 2. The perforated film may lie in a first geometrical plane 340. Thus, similarly to FIG. 2, if the perforated film 332 is coated with an adhesive layer at the central inspection area, the perforation would also extend through the adhesive layer, which together with the film 332 would form a perforated body contact layer. However, contrary to the central inspection area 212 of FIG. 2, which is defined by the inner perimeter of the border area 204, the central inspection area 312 of FIG. 3a is defined by a raised wall portion 310 (which is similar to the raised wall 110 portion of FIG. 1). The raised wall portion 310 may be at least partially defined by an annular border area 304. The raised wall portion 320 may lie in a second geometrical plane 342 proejcted distally from, and parallel with, the first geometrical plane 340 along a distance d. The embodiment illustrated in FIG. 3b has also a raised wall portion 310.

In each one of the embodiments illustrated in FIGS. 3a and 3b, the removable pad 302 is provided with two attachment means 314, for attaching the pad 302 to the wall portion 310 and keeping the pad 302 in its first state, i.e. the state in which the pad 302 and the medical dressing 300a, 300b is used for reducing the risk of pressure ulcers developing. One or both of the two attachment means 314 may be detached from the wall portion 310 to allow tilting or complete removal of the pad (i.e. arriving at its second state), whereby the central inspection area 312 may be visually inspected.

In the illustrated embodiments in FIGS. 3a and 3b, when the pad 302 is properly placed in the central inspection area 312 in its first state, the geometrical axis of symmetry X or the plane of symmetry of the pad 302 will extend through the attachment means 314. However, in other embodiments the attachment means 314 may be arranged off-center compared to the axis or plane of symmetry X.

The embodiment illustrated in FIG. 3b differs from the embodiment illustrated in FIG. 3a in that the central inspection area 312 is a through hole defined by the wall portion 310, i.e. it is void of any film or other material extending across the central inspection area 312.

In the embodiments illustrated in FIGS. 3a and 3b the thickness of the pad 302 may suitably correspond to the height of the raised wall portion 310 which defines the hole in the form of the central inspection area. In such embodiments, in the first state, the distal side of the pad 302 may suitably be level with the distal side of the raised wall portion 310. This may be advantageous from production purposes, as the wall portion 310 and the pad 302 may be provided from a single-piece blank. Although the entire pad may suitably be made to fit into the hole, in other embodiments, it is conceivable that part of the pad 302 extends distally to the raised wall portion 310. In such case, only part of the pad 302 would be sunk into the hole, when in said first state. Another such example is the medical dressing 200 in FIG. 2, in which the hole and central inspection area 212 is defined by the border area 204. Since the border area 204 is relatively thin, only part of the relatively thicker pad 202 will be sunk into the hole, when in said first state. Nevertheless, in each of these cases, because the pad is sunk into the hole/central inspection area, the pad may come close to (e.g. in case of blind hole) or in direct contact with (e.g. in case of through hole) the skin of the patient, thereby enabling a pressure relieving function.

The embodiments illustrated in FIGS. 3a and 3b may form part of a medical dressing system. Such as system comprises the medical dressing 300a or 300b. The pad 302 may either be provided/packaged in a pre-assembled state, i.e. in said first state, or it may be provided/packaged as a separate component for subsequent placement in said first state. Furthermore, the pad 302 illustrated in FIGS. 3a and 3b may be a first pad, wherein the system further comprises a replacement pad for replacing the first pad 302 while the medical dressing 300a, 300b is still applied to a human body without requiring removal of the border area from the skin of the body.

While the embodiments illustrated in FIGS. 1-3b are particularly suitable for being applied to the gluteal cleft, it should be understood that the general inventive concept could be realized for other parts of a human body. For instance, a medical dressing may be configured and dimensioned to be applied to a knee, elbow, heel, etc, the latter being illustrated in FIG. 4.

Figure 4:
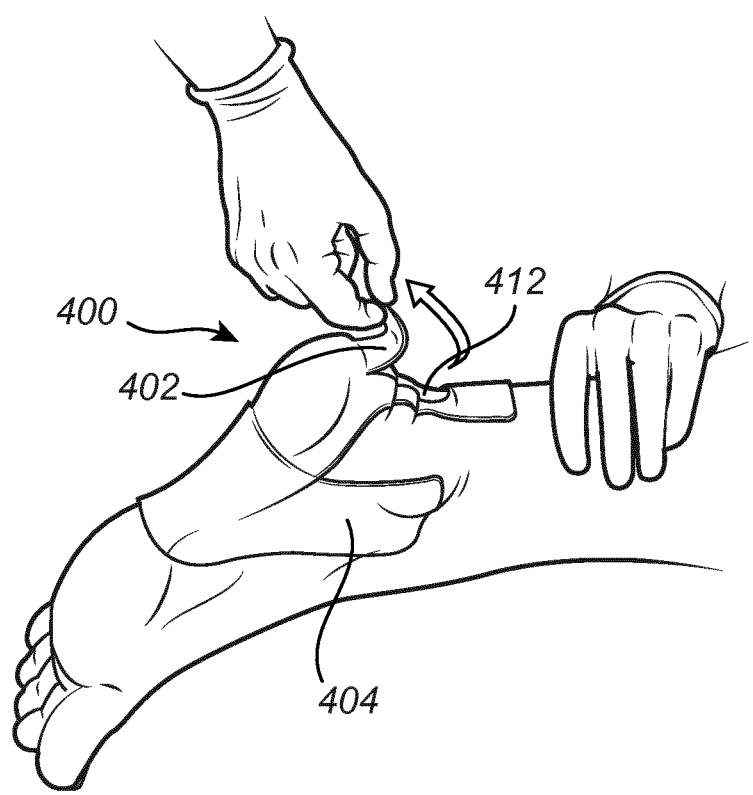
FIG. 4 shows a medical dressing according to at least one other exemplary embodiment of the invention.

FIG. 4 shows a medical dressing 400 according to at least one other exemplary embodiment of the invention. The medical dressing 400 is adapted to be placed on a heel of a human body. For keeping the medical dressing 400 in place, the medical dressing 400 does not only cover the heel but also extends across the foot sole, from which the adhesive border area 404 extends upwardly on both the medial and the lateral side of the foot. The pad 402 of the medical dressing 400 is herein illustrated as being located at least on the posterior side of the heel. Similarly to the other discussed embodiments, the pad 402 may be at least partly removed to uncover the central inspection area 412 for enabling visual inspection of the treatment area of the heel. Although a border area for the medical dressing 400 will have a different contour to fit the heel, rather than for example the gluteal cleft, it should be understood that such contours are also considered in this application to be annular. For instance, for a medical dressing 400 adapted for the heel the annular border area may have a butterfly-like contour. It should be understood that the various structural features of the medical dressings in FIGS. 1a-3 could be implemented in a medical dressing for any part of the human body, such as for the heel as illustrated in FIG. 4. Such structural features include, but are not limited to, the layers of the medical dressing, the attachment means, the presence or absence of a raised wall portion, the film of the border area extending across the central inspection area, etc.

The invention claimed is:

1. A medical dressing for application at a treatment area of a human body for reducing the risk of pressure sores, comprising:

(a) an annular border area surrounding (b) a central inspection area, the annular border area and the central inspection area formed of a perforated film, the perforated film having a body-facing proximal side and an opposite distal side, wherein perforations of the perforated film extend between the body-facing proximal side and the opposite distal side, the perforated film of the annular border area comprising:
—the body-facing proximal side provided with an adhesive layer for adhering the annular border area to skin surrounding said treatment area; and
—a backing layer applied to the opposite distal side of the perforated film, covering the perforations, wherein the central inspection area is for alignment with said treatment area, wherein the central inspection area is defined by a raised wall portion which is surrounded by said annular border area, wherein said perforated film lies in a first geometrical plane and the raised wall portion projects distally from said first geometrical plane, wherein the raised wall portion at least partly defines a frame around said central inspection area, wherein a thickness of the annular border area is smaller than a thickness of the raised wall portion, wherein a distal end surface of said raised wall portion and a distal end surface of a pad lie in a common second geometrical plane, said second geometrical plane being parallel with said first geometrical plane, wherein the central inspection area comprises an opening that is a blind hole, a bottom of the blind hole being formed by said perforated film that extends into and across the central inspection area, wherein the perforations across the central inspection area allow moisture to be transported away from the skin, (c) said pad positionable within the central inspection area, the pad movable between at least two states:
—a first state in which the pad is located in the central inspection area, positioned over the perforated film and is positioned within the central inspection area such that a proximate end surface of said pad contacts the perforated film of the central inspection area for providing a pressure relieving function; and
—a second state in which the pad is at least partly removed from the central inspection area for enabling visual inspection of said treatment area, and wherein the pad further comprises:
—a first absorbent layer comprising a foam material;
—a second absorbent layer comprising a superabsorbent material; and wherein an adhesive strength between the pad and the perforated film is between 1 N/25 mm and 3 N/25 mm.

2. The medical dressing as claimed in claim 1, wherein the medical dressing is adapted for placement on a sacral area of the human body, wherein the medical dressing has a geometrical axis of symmetry, wherein the border area comprises a first lobed portion on one side of said axis of symmetry and a second lobed portion on the other side of said axis of symmetry.

3. The medical dressing as claimed in claim 2, wherein said pad is a first pad, the medical dressing further comprising a replacement pad for replacing the first pad while the medical dressing is still applied to the human body without requiring removal of the border area from the skin of the body.

4. The medical dressing of claim 1, wherein the pad further comprises a liquid distributing layer positioned between the first absorbent layer and the second absorbent layer for transmitting liquid absorbed by the first absorbent layer to the second absorbent layer.

5. The medical dressing of claim 4, wherein the liquid distributing layer comprises a non-woven material.

6. The medical dressing as claimed in claim 1, wherein said border area defines a boundary of said central inspection area.

7. The medical dressing as claimed in claim 1, wherein said pad is attached or attachable to said wall portion at least in said first state.

8. The medical dressing as claimed in claim 1, wherein said pad is provided with releasable attachment for attaching said pad to said wall portion, wherein releasing said attachment enables the pad to be moved from said first state to said second state of the pad, wherein the attachment allows re-attachment of said pad to said wall portion when said pad is moved back to said first state.

9. The medical dressing as claimed in claim 1, wherein said pad is a cutout from said raised wall portion.

10. The medical dressing as claimed in claim 1, wherein said raised wall portion defines a central hole included in said central inspection area.

11. The medical dressing as claimed in claim 1, wherein said pad is provided in said first state or as a separate component for subsequent placement in said first state.

12. A method of reducing workload for nursing personnel, comprising providing a replacement pad for enabling the nursing personnel to replace a used pad comprised in the medical dressing as claimed in claim 1 or in the medical dressing as claimed in claim 11 with said replacement pad, without requiring removal of the border area from the skin of the body.

13. The medical dressing of claim 1, wherein at least one of the first absorbent layer or the second absorbent layer has a maximum absorptive capacity of at least three times its own weight as measured by EN 13726-1:2002.

14. A medical dressing for application at a treatment area of a human body, comprising:
(a) an annular border area surrounding (b) a central inspection area,
the annular border area and the central inspection area formed of a perforated film, the perforated film having a body-facing proximal side and an opposite distal side, wherein perforations of the perforated film extend between the body-facing proximal side and the opposite distal side,
the perforated film of the annular border area comprising:
—the body-facing proximal side provided with an adhesive layer for adhering the annular border area to skin surrounding said treatment area; and
—a backing layer applied to the opposite distal side of the perforated film, covering the perforations,
wherein the central inspection area is for alignment with said treatment area,
wherein the central inspection area defines an opening, and wherein the perforated film extends across the opening of the central inspection area, wherein the perforations across the central inspection area allow moisture to be transported away from the skin; and
(c) a pad movable between at least two states:
—a first state in which the pad is located in the central inspection area positioned over the perforated film such that a proximate end surface of the pad contacts the perforated film of the central inspection area for providing a pressure relieving function; and
—a second state in which the pad is at least partly removed from the central inspection area for enabling visual inspection of said treatment area, wherein the central inspection area is defined by a raised wall portion which is surrounded by said annular border area, wherein said perforated film lies in a first geometrical plane and the raised wall portion projects distally from said first geometrical plane, wherein the raised wall portion at least partly defines a frame around said central inspection area, wherein a thickness of the annular border area is smaller than a thickness of the raised wall portion, wherein a distal end surface of said raised wall portion and a distal end surface of said pad lie in a common second geometrical plane, said second geometrical plane being parallel with said first geometrical plane, wherein the annular border area perforated film forms an outer perimeter of the medical dressing that is thinner than the pad, and wherein the pad further comprises:
   —a first absorbent layer comprising a foam material;
   —a second absorbent layer comprising a superabsorbent material; and
   —a liquid distributing layer positioned between the first absorbent layer and the second absorbent layer, wherein the liquid distributing layer comprises a non-woven material,
wherein an adhesive strength between the pad and the perforated film is between 1 N/25 mm and 3 N/25 mm.

* * * * *